United States Patent
Bi

(10) Patent No.: US 10,466,161 B1
(45) Date of Patent: Nov. 5, 2019

(54) DEFINED SHEAR RATE CORROSION TESTER

(71) Applicant: Hongfeng Bi, Houston, TX (US)

(72) Inventor: Hongfeng Bi, Houston, TX (US)

(73) Assignee: Hongfeng Bi, Houston, TX (US)

( * ) Notice: Subject to any disclaimer, the term of this patent is extended or adjusted under 35 U.S.C. 154(b) by 173 days.

(21) Appl. No.: 15/670,483

(22) Filed: Aug. 7, 2017

(51) Int. Cl.
*G01N 17/00* (2006.01)
*G01N 17/04* (2006.01)

(52) U.S. Cl.
CPC .......... *G01N 17/04* (2013.01); *G01N 17/006* (2013.01)

(58) Field of Classification Search
CPC ...................................... G01N 17/04
USPC .......................................... 436/34
See application file for complete search history.

(56) References Cited

U.S. PATENT DOCUMENTS

| | | | |
|---|---|---|---|
| 2,405,532 A | 8/1946 | Todd et al. | |
| 2,519,323 A | 8/1950 | Shank et al. | |
| 3,116,977 A | 1/1964 | Grabowski et al. | |
| 3,936,273 A | 2/1976 | Powell | |
| 4,092,122 A | 5/1978 | Suga et al. | |
| 6,077,418 A | 6/2000 | Iseri et al. | |
| 6,951,127 B1 * | 10/2005 | Bi | G01N 11/162 73/54.01 |
| 8,261,601 B2 * | 9/2012 | Stolle | G01N 25/56 422/53 |
| 8,513,020 B2 | 8/2013 | Hehn et al. | |
| 8,813,542 B1 * | 8/2014 | Bi | G01N 11/14 73/54.23 |

* cited by examiner

*Primary Examiner* — Christine T Mui
*Assistant Examiner* — Emily R. Berkeley

(57) ABSTRACT

The present invention pertains to method and apparatus for determining corrosion rate or loss of metal, due to chemical reaction with a corrosive testing fluid under defined shear rate and varied pressure and temperature conditions. This apparatus features a coaxially positioned cylindrical shaped rotating cup and a static cylindrical coupon, or a static cylindrical cup and a rotating coupon located in a test chamber. This defined shear rate corrosion tester can rotate various speeds through a magnetic drive mechanism. Due to its configuration, the corrosion tester is easy to couple with different kinds of testing chambers on demand, and it requires low maintenance and ease of cleaning.

14 Claims, 2 Drawing Sheets

DEFINED SHEAR RATE CORROSION TESTER

BACKGROUND

Field of Invention

The present invention pertains to method and apparatus for determining corrosion rate or loss of metal, due to chemical reaction with a corrosive testing fluid under defined shear rate and varied pressure and temperature conditions. It features a coaxially positioned cylindrical shaped rotating cup and a static cylindrical coupon, or a static cylindrical cup and a rotating coupon located in a test chamber. The defined shear rate corrosion tester can rotate various speeds through a magnetic drive mechanism.

Description of Prior Art

The function of drilling fluid is primarily removal drilling cuttings from borehole. Besides, other requirement are expected of drilling fluid, such as cool, clean, lubricate drilling bit and drilling string, maintain hole stability, prevent inflow of formation fluids, etc. Therefore, the drilling fluid must be safe for both personal and formation environment. The corrosive of drilling fluid is a particularly important factor that has to be controlled. It has been recognized to be the major cause of drilling pipe failure and damage to drilling fluid circulation equipment. Corrosion test under defined shear rate is used to study corrosion damage regarding to drilling pipe eccentricity and drill pipe rotation. Additionally, in order to improve oil recovery, acid fluids are pumped into production well to react with rock in order to improve rock porosity and formation connectivity. Corrosion control is difficult in high pressure and high temperature environment, but it can be significantly reduced through simulation experiment and prevention procedure.

U.S. Pat. No. 2,405,532 introduces an apparatus for conducting corrosion tests on specimens of base metals, metal alloys, metal sheathed, etc. This apparatus has a jacketed test chamber that uniformly heats the humidified atmosphere within test chamber and allows a desired constant internal temperature to be maintained. The test chamber can test multiple specimens at a time for the purpose of comparison. These testing samples are not limited to one size. However, this apparatus only tests specimens in the presence of corrosion-producing vapors and does not allow the testing of corrosion-producing liquids.

U.S. Pat. No. 2,519,323 presents a method and apparatus of measuring the eroding and corroding effect of a fluid on a solid material, which comprises rotating a hollow cylindrical body of the solid material in a quantity of the fluid, and weighting the solid material force and after the exposure to the fluid. The corrosion-producing fluid may be a liquid, gas, emulsion, etc. Samples may be exposed to different fluid velocities by the rotation of the spindle. However, only one sample can be tested at a time, and there are no pressure and temperature controls in liquid bath of corrosion-producing fluid.

U.S. Pat. No. 3,116,977 brings an apparatus that reciprocates samples in the steam to test the effectiveness of inhibitors that are dissolved in the boiling water to prevent stress corrosion cracking of samples during the evaporating region. Samples are heated by a source of electrical potential at a temperature above the boiling water's temperature to allow the quick evaporation of the liquid on the samples. However, this apparatus can't measure the effectiveness of inhibitors under defined shear rate or varied pressure and temperature conditions.

U.S. Pat. No. 3,936,273 introduces an apparatus that consists of a housing, a mountable axial shaft, a heating element and a driving motor. The sealable housing contains a test fluid in a predetermined environment. Test specimens are mounted on the shaft and rotated in partially immersed emplacement within bath. The samples are weighted before and after exposure to test fluid to determine the corrosion of the samples. However, test specimens are partially immersed within bath, and there is no pressure control or shear rate control in bath of test fluid.

U.S. Pat. No. 4,092,122 presents a spray cabinet type of corrosion test machine. Specimens are mounted on a supporting column and rotated around a spraying tower. The testing chamber can test multiple specimens at a time for comparing. However, spray particle size is a variable which is difficult to control. This machine can't test corrosion under defined shear rate or varied pressure and temperature conditions.

U.S. Pat. No. 6,077,418 introduces a method of monitoring corrosion of a test coupon under heat transfer condition. The corrosion of the metal member is monitored based on measuring electrical signals between the test coupon and the electrode immersed in the corrosive fluid. However, this method can't measure the corrosion rate under defined shear rate or varied pressure and temperature conditions.

U.S. Pat. No. 8,513,020 brings a method and apparatus of corrosion testing. It comprises an enclosed testing chamber containing a fluid bath saturated with a corrosive gas. A testing specimen is mounted in a test assembly that applies a four point bending test when the testing specimen is submerged in the corrosive fluid. However, this method allows only one sample to be tested at a time, and corrosive fluid may only be static.

It is an object of this invention to provide a practical and affordable method for accurately measuring corrosion rate of testing samples without compromising its integrity and performance.

It is another object of this invention to determine corrosion rate or loss of metal under defined shear rate which requires substantially less maintenance work than other designs yet meet industry standards of accuracy, repeatability, durability, and ease of cleaning.

SUMMARY OF THE PRESENT INVENTION

The present invention pertains to methods and apparatus for determining corrosion rate or loss of metal, due to chemical reaction with the corrosive testing fluid under defined shear rate and varied pressure and temperature conditions. It features a coaxially positioned cylindrical shaped rotating cup and a static cylindrical coupon, or a static cylindrical cup and a rotating coupon located in a test chamber. The defined shear rate corrosion tester can rotate various speeds through a magnetic drive mechanism. Due to its configuration, the corrosion tester is easy to couple with different kinds of testing chambers on demand, and it requires low maintenance and ease of cleaning.

DRAWING FIGURES

Other objects, features and advantages will be apparent from the following detailed descriptions of embodiment taken in conjunction with accompanying drawing in which.

Figure 1:
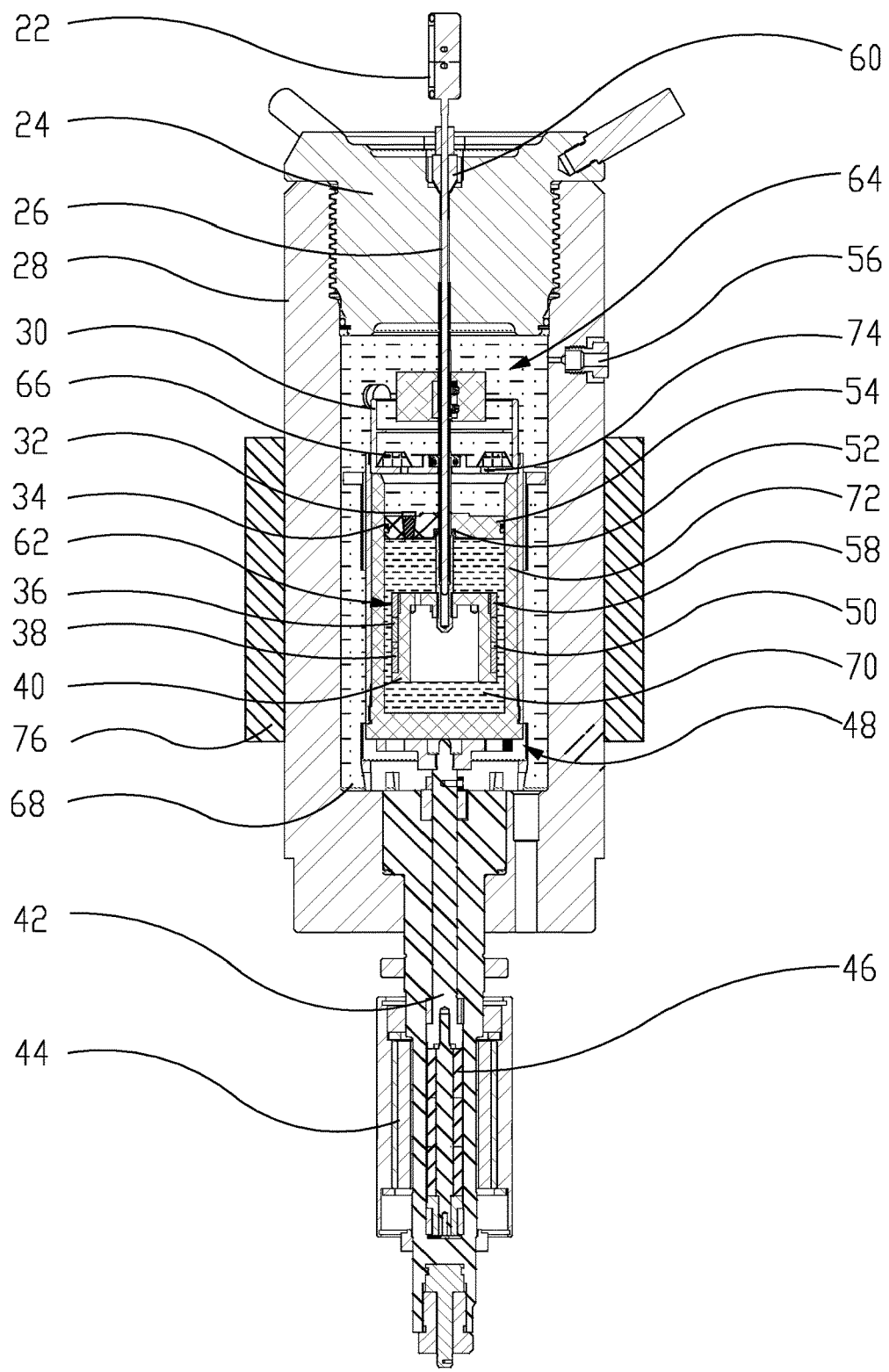
FIG. 1 is a cross sectional view of corrosion tester installed in a bottom magnetic drive test chamber.

| REFERENCE NUMERALS IN DRAWINGS | | | |
|---|---|---|---|
| 22 | Thermocouple | 24 | Cap |
| 24A | Cap | 26 | Shaft |
| 26A | Shaft | 28 | Test chamber |
| 28A | Test chamber | 30 | Lid |
| 30A | Lid | 32 | Screw |
| 32A | Screw | 34 | O-ring |
| 34A | O-ring | 36 | First corrosion coupon |
| 36A | First corrosion coupon | 38 | Second corrosion coupon |
| 38A | Second corrosion coupon | 40 | Bob base |
| 40A | Bob base | 42 | Shaft |
| 44 | Outside magnet | 44A | Outside magnet |
| 46 | Inside magnet | 46A | Inside magnet |
| 48 | Cup assembly | 48A | Cup assembly |
| 50 | Spacer | 50A | Spacer |
| 52 | Dynamic seal | 52A | Dynamic seal |
| 54 | Piston | 54A | Piston |
| 56 | Pressurization port | 56A | Pressurization port |
| 58 | Bob nut | 58A | Bob nut |
| 60 | Nut | 62 | Bob assembly |
| 62A | Bob assembly | 64 | Corrosion Tester |
| 64A | Corrosion Tester | 66 | Sacrificial material |
| 66A | Sacrificial material | 68 | Pressurization fluid |
| 68A | Pressurization fluid | 70 | Sample fluid |
| 70A | Sample fluid | 72 | Liner |
| 72A | Liner | 74 | Opening |
| 74A | Opening | 76 | Heater |
| 76A | Heater | 28 | Test chamber |

DESCRIPTION—FIG. 1—PREFERRED EMBODIMENT

Referring to FIG. 1, a defined shear rate corrosion tester comprises a corrosion tester 64 and a test chamber 28 with a bottom magnetic drive system. Corrosion tester 64 includes a cup assembly 48 and a bob assembly 62. Cup assembly 48 has a Teflon liner 72 to contain a corrosive sample fluid 70. Bob assembly 62 comprises a ring shaped first corrosion coupon 36 and a ring shaped second corrosion coupon 38 separated by a spacer 50 mounted on a bob base 40 and held in place by a bob nut 58. First corrosion coupon 36 and second corrosion coupon 38 may be made of different types of materials to test at the same time. Bob assembly 62 and a piston 54 are attached to a shaft 26. A dynamic seal 52 and an O-ring 34 are installed on piston 54. A seal screw 32 is positioned on top of piston 54 to prevent the corrosive testing fluid from leaking. A lid 30 is installed to secure liner 72 inside of cup assembly 48. A sacrificial material 66 on top of lid 30 is used to react with corrosive sample fluid 70 leaking out of cup assembly 48 in order to protect other components from corrosion. Test chamber 28 is sealed by a cap 24. An outside magnet 44 and an inside magnet 46 are coupling together to drive cup assembly 48 to rotate through a shaft 42, while bob assembly 62 remains static. A nut 60 is installed on top of cap 24 to secure a thermocouple 22 in order to measure testing temperature. A pressurization fluid 68 is injected through a pressurization port 56 and enters corrosion tester 64 through an opening 74 to maintain desired testing pressure.

OPERATION—FIG. 1—PREFERRED EMBODIMENT

Weight first corrosion coupon 36 and second corrosion coupon 38 to determine initial weight. Slide second corrosion coupon 38 onto bob base 40, followed by spacer 50, first corrosion coupon 36, and bob nut 58. Attach O-ring 34 to piston 54. Insert dynamic seal 52 into the center hole of piston 54 on the side that will face bob assembly 62.

Pour desired amount of sample fluid 70 into cup assembly 48. Then, attach bob assembly 62 to the base of shaft 26. Install piston 54 onto shaft 26. Insert shaft 26 into cup 48 assembly and submerge bob assembly 62 into sample fluid 70. Insert screw 32 into piston 54, but do not tighten. Press piston 54 down until the corrosive fluid can be seen bleeding through the screw hole, and then tighten screw 32. Close cup assembly 48 with lid 30, and put sacrificial material 66 on top of lid 30. Insert corrosion tester 64 into test chamber 28 that provides pressure and temperature control of sample fluid 70. To generate defined shear rate, test chamber 28 drives cup assembly 48 to rotate by the bottom magnetic drive system, while bob assembly 62 remains static. Shear rate is controlled by controlling the rotation speed of cup assembly 48. Pressure is controlled by adding or subtracting pressurization fluid 68 through pressurization port 56. Temperature is controlled by heating or cooling test chamber 28 through a heater. Piston 54 will move up and down to accommodate the volume changes of sample fluid 70 while keeping sample fluid 70 contained. After running the test, remove and disassemble corrosion tester 64. Remove bob assembly 62 from shaft 26 and remove first corrosion coupon 36 and second corrosion coupon 38 from bob base 40. Clean and weigh first corrosion coupon 36 and second corrosion coupon 38 to determine corrosion rate. Alternatively, corrosion rate can be measured by analyzing composition changes of sample fluid 70, or other means.

DESCRIPTION—FIG. 2—ALTERNATIVE EMBODIMENT

Figure 2:
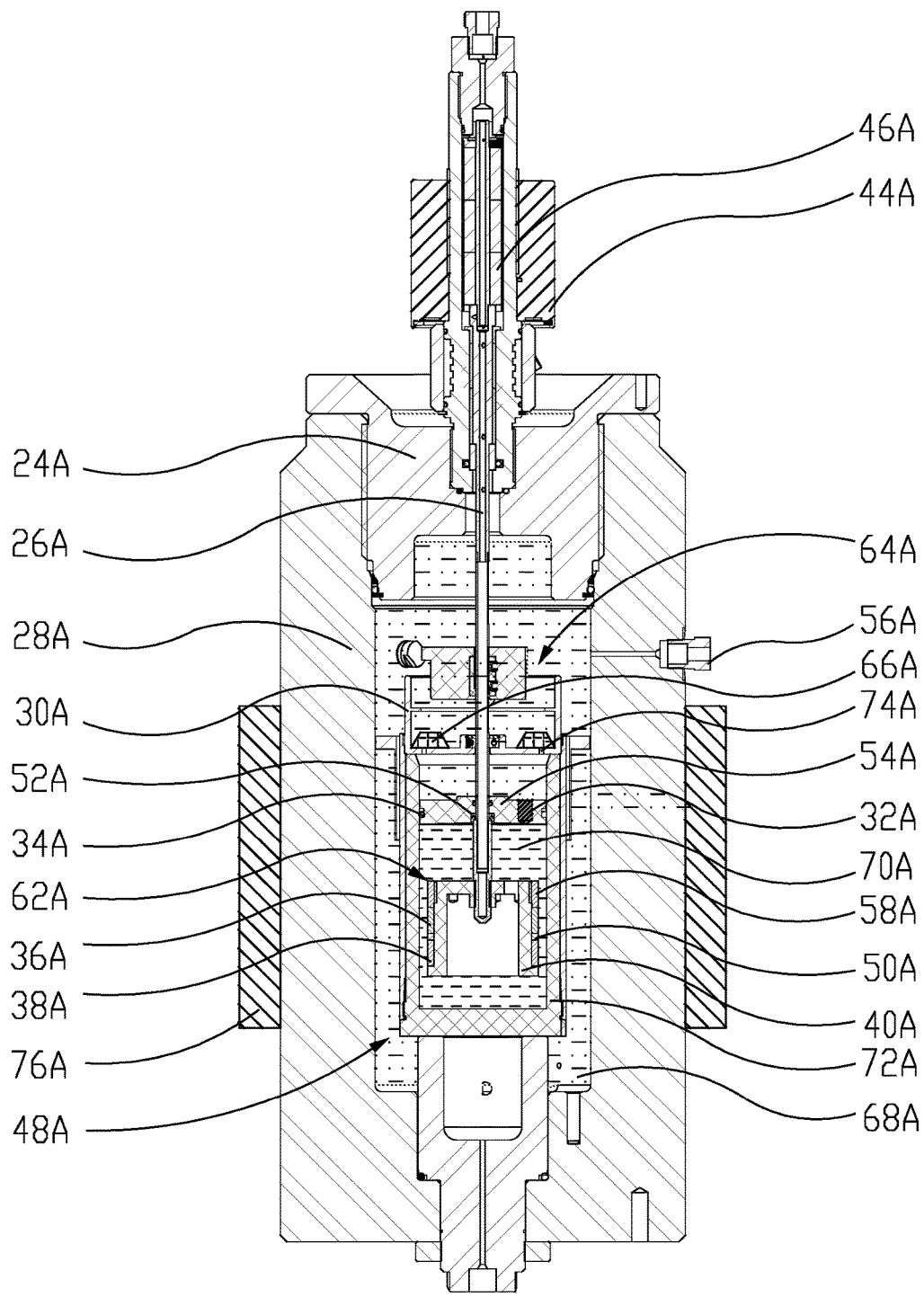
FIG. 2 is a cross section view of corrosion tester installed in a top magnetic drive test chambers.

FIG. 2 shows that a defined shear rate corrosion tester comprises a corrosion tester 64A and a test chamber 28A with a top magnetic drive system. Corrosion tester 64A includes a cup assembly 48A and a bob assembly 62A. Cup assembly 48A has a Teflon liner 72A to contain a corrosive sample fluid 70A. Bob assembly 62A comprises a ring shaped first corrosion coupon 36A and a ring shaped second corrosion coupon 38A separated by a spacer 50A mounted on a bob base 48A and held in place by a bob nut 58A. First corrosion coupon 36A and second corrosion coupon 38A may be made of different types of materials to test at the same time. Bob assembly 62A and a piston 54A are attached to a shaft 26A. A dynamic seal 52A and an O-ring 34A are installed on piston 54A. A seal screw 32A is positioned on top of piston 54A to prevent the corrosive sample fluid 70A from leaking. A lid 30A is installed to secure liner 72A inside of cup assembly 48A. A sacrificial material 66A on top of lid 33A is used to react with corrosive sample fluid 70A leaking out of cup assembly 48A in order to protect other components from corrosion. Test chamber 28A is sealed by a cap 24A. An outside magnet 44A and an inside magnet 46A are coupling together to drive bob assembly 62A to rotate through shaft 26A, while cup assembly 48A remains static. A pressurization fluid 68A is injected through a pressurization port 56A and enters corrosion tester 64A through an opening 74A to maintain desired testing pressure.

OPERATION—FIG. 2—ALTERNATIVE EMBODIMENT

Weight first corrosion coupon 36A and second corrosion coupon 38A to determine initial weight. Slide second corrosion coupon 38A onto bob base 40A, followed by spacer 50A, first corrosion coupon 36A, and bob nut 58A. Attach O-ring 34A to piston 54A. Insert dynamic seal 52A into the center hole of piston 54A on the side that will face bob assembly 62A. Insert O-ring 34A into the hole on the opposite side of piston 54A.

Pour desired amount of the corrosive testing fluid into cup assembly 48A. Then, attach bob assembly 62A to the base of shaft 26A. Install piston 54A onto shaft 26A. Insert shaft 26A into cup assembly 48A and submerge bob assembly 62A into sample fluid 70A. Insert screw 32A into piston 54A, but do not tighten. Press piston 54A down until sample fluid 70A can be seen bleeding through the screw hole, and then tighten screw 32A. Close cup assembly 48A with lid 30A, and put sacrificial material 66A on top of lid 30A. Insert corrosion tester 64A into test chamber 28A that provides pressure and temperature control of sample fluid 70A. To generate defined shear rate, test chamber 28A drives bob assembly 62A to rotate by the top magnetic drive system, while cup assembly 48A remains static. Shear rate is controlled by controlling the rotation speed of bob assembly 62A. Pressure is controlled by adding or subtracting pressurization fluid 68A through pressurization port 56A. Temperature is controlled by heating or cooling test chamber 28A through a heater 76A. Piston 54A will move up and down to accommodate the volume changes of sample fluid 70A while keeping sample fluid 70A contained. After running the test, remove and disassemble corrosion tester 64A. Remove bob assembly 62A from shaft 26A and remove first corrosion coupon 36A and second corrosion coupon 38A from bob base 40A. Clean and weigh first corrosion coupon 36A and second corrosion coupon 38A to determine corrosion rate. Alternatively, corrosion rate can be measured by analyzing composition changes of sample fluid 70A, or other means.

CONCLUSION, RAMIFICATIONS, AND SCOPE

Accordingly, the reader will see a corrosion tester used to determine corrosion rate, or loss of metal due to chemical reaction under defined shear rate and different pressure and temperature conditions.

A ramification of the preferred embodiment is that cup assembly 48 could be shaped like a square, an oval, or other shapes as well.

Another ramification of the preferred embodiment is that corrosion coupons could be shaped like a square, an oval, or other shapes as well.

Another ramification of the preferred embodiment is that corrosion coupons could be made of different materials, such as metal, plastic, etc.

Another ramification of the preferred embodiment is that drive system doesn't have to be magnetic drive. It could be a direct drive through gear, pulley belt, etc.

Another ramification of the preferred embodiment is that measuring the chemical composition change of sample fluid 70 can also be used to evaluate the corrosion rate of first corrosion coupon 36 and second corrosion coupon 38.

It will be apparent to those skilled in the art that other embodiments, improvements, details, and uses can be made consistent with letter and spirit of the foregoing disclosure and within the scope of this patent, which is limited only by the following claims, construed in accordance with the patent law, including, the doctrine of equivalents.

OBJECTS AND ADVANTAGES

From the description above, a number of advantages of present invention become evident:

a. Very economically measuring corrosion rate or metal loss on demand, by test chamber with different shear rate, pressure and temperature ratings.
b. Due to the limited number of components and configuration, the current invention is easy to manufacture, operate and requires low maintenance.

Further objects and advantages of my invention will become apparent from a consideration of the drawings and ensuing descriptions.

What I claimed:

1. A corrosion tester instrument used to determine corrosion rate or metal loss due to chemical reaction under defined shear rate, including:
    (a) a cylindrical testing coupon,
    (b) a cylindrical sample cup coaxially located respect to said cylindrical testing coupon,
    (c) a corrosive testing fluid contained in said cylindrical sample cup,
    (d) a means to drive said cylindrical sample cup to rotate while keep said cylindrical testing coupon static and said cylindrical testing coupon's outer surface is submerged in said corrosive testing fluid,
    (e) a means to determine the reaction rate between said cylindrical testing coupon and said corrosive testing fluid.

2. The instrument of claim 1 wherein said cylindrical sample cup has a corrosion resistant liner.

3. The instrument of claim 1 further comprises a sacrificial material to prevent said corrosive testing fluid from reacting with components outside said cylindrical sample cup.

4. The instrument of claim 1 wherein said means to drive said cylindrical sample cup is a magnetic drive system.

5. The instrument of claim 1 further comprises a floating piston installed above said cylindrical testing coupon.

6. The instrument of claim 1 further comprises a pressurization medium to pressurize said corrosive testing fluid.

7. The instrument of claim 1 further comprises a heater to provide temperature control of said corrosive testing fluid.

8. A corrosion tester instrument used to determine corrosion rate or metal loss due to chemical reaction under defined shear rate, including:
    a) a cylindrical testing coupon,
    b) a cylindrical sample cup coaxially located respect to said cylindrical testing coupon,
    c) a corrosive testing fluid contained in said cylindrical sample cup,
    d) a means to drive said cylindrical sample cup to rotate while said cylindrical testing coupon is static and said cylindrical testing coupon's outer surface is submerged in said corrosive testing fluid,
    e) a floating piston installed above said cylindrical testing coupon to contain said corrosive testing fluid.

9. The instrument of claim 8 wherein said cylindrical sample cup has a corrosion resistant liner.

10. The instrument of claim 8 further comprises a sacrificial material to prevent said corrosive testing fluid from reacting with components outside said cylindrical sample cup.

11. The instrument of claim 8 wherein said means to drive said cylindrical sample cup is a magnetic drive system.

12. The instrument of claim 8 further comprises a pressurization medium to pressurize said corrosive testing fluid.

13. The instrument of claim 8 further comprises a means to determine reaction rate.

14. The instrument of claim 13 wherein said means to determine reaction rate is to analyze the chemical composition change of said corrosive testing fluid.

* * * * *